United States Patent
Heimdal

(10) Patent No.: US 11,664,113 B2
(45) Date of Patent: May 30, 2023

(54) METHODS AND SYSTEMS FOR VISUALLY DETECTABLE PROCESSING INDICATORS

(71) Applicant: GE Precision Healthcare LLC, Milwaukee, WI (US)

(72) Inventor: Andreas Heimdal, Oslo (NO)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

(21) Appl. No.: 17/450,437

(22) Filed: Oct. 8, 2021

(65) Prior Publication Data

US 2023/0115718 A1 Apr. 13, 2023

(51) Int. Cl.
| | | |
|---|---|---|
| *G06T 11/40* | (2006.01) | |
| *G16H 40/40* | (2018.01) | |
| *G16H 30/20* | (2018.01) | |
| *G16H 40/60* | (2018.01) | |
| *G06T 19/00* | (2011.01) | |

(52) U.S. Cl.
CPC ............ *G16H 30/20* (2018.01); *G06T 11/40* (2013.01); *G06T 2210/41* (2013.01)

(58) Field of Classification Search
CPC ... G06T 11/40; G06T 2210/41; G06T 19/006; G06T 2207/10072; G06T 2207/10068; G06T 2207/10136; G06T 2019/2012; G16H 30/20; G16H 40/40; G16H 40/60; A61B 8/54
USPC ....................................................... 345/589
See application file for complete search history.

(56) References Cited

U.S. PATENT DOCUMENTS

| | | | |
|---|---|---|---|
| 6,147,607 A | 11/2000 | Lynn | |
| 6,485,979 B1 | 11/2002 | Kippenhan et al. | |
| 9,339,253 B2 | 5/2016 | Peszynski et al. | |
| 10,957,442 B2 * | 3/2021 | Kalafut | G16H 50/20 |
| 11,172,908 B2 * | 11/2021 | Yardi | A61B 6/4208 |
| 2012/0116803 A1 | 5/2012 | Reid et al. | |
| 2017/0232125 A1 | 8/2017 | Carling | |

(Continued)

FOREIGN PATENT DOCUMENTS

JP   WO 2018066429 A1 * 9/2017 ............ G16H 40/40

OTHER PUBLICATIONS

Stipe, D., "Color in Medical Products," Forma Medical Device Design Website, Available Online at https://www.formamedicaldevicedesign.com/white-papers/color-medical-products/, Available as Early as Mar. 5, 2016, 21 pages.

(Continued)

*Primary Examiner* — Wesner Sajous
(74) *Attorney, Agent, or Firm* — McCoy Russell LLP

(57) ABSTRACT

Various methods and systems are provided for conveying information about cleaning, disinfection, and sterilization (e.g., processing) of touchable components of a medical device using visually detectable indicators (VDIs). Information regarding processing of an ultrasound device may be conveyed by configuring the ultrasound device to include a first component with a first visual indicator to indicate a first processing level and a second component with a second visual indicator to indicate a second processing level. Implementing visual indicators to convey information about processing may reduce time, cost, and other resources used to process medical devices compared to conventional processing methods wherein the entire medical device may be processed to one processing level.

16 Claims, 8 Drawing Sheets

(56) References Cited

U.S. PATENT DOCUMENTS

| | | |
|---|---|---|
| 2017/0304467 A1 | 10/2017 | Daneluzzi et al. |
| 2018/0055593 A1* | 3/2018 | Schlatterer |
| 2019/0201073 A1* | 7/2019 | Nott ........................ A61B 34/30 |
| 2020/0205750 A1* | 7/2020 | Begin ..................... A61B 5/743 |
| 2021/0015456 A1* | 1/2021 | Chiang ................ A61B 8/0883 |
| 2021/0192759 A1* | 6/2021 | Lang ....................... A61B 34/25 |
| 2021/0251538 A1* | 8/2021 | Muhsin .................. G16H 40/63 |
| 2022/0343609 A1* | 10/2022 | Devam ................... G06T 15/02 |

OTHER PUBLICATIONS

"Quality System Regulation Labeling Requirements," FDA Website, Available Online at https://www.fda.gov/medical-devices/device-labeling/quality-system-regulation-labeling-requirements, Available as Early as Aug. 31, 2018, 9 pages.

* cited by examiner

METHODS AND SYSTEMS FOR VISUALLY DETECTABLE PROCESSING INDICATORS

FIELD

Embodiments of the subject matter disclosed herein relate to processing (e.g., cleaning, disinfecting, sterilizing) of ultrasound devices.

BACKGROUND

Medical equipment is often used in environments where there is a need for processing. Processing may include five cleaning/disinfection/sterilization (CDS) levels, including cleaning, low level disinfection, intermediate level disinfection, high level disinfection, and sterilization. Medical equipment, for example, an ultrasound device, may include touchable components made of different surface materials and having different uses and use frequencies. A surface material, a use, and a use frequency of a component of the ultrasound device may determine an appropriate level and frequency of processing for the component. Some components of the ultrasound device may only sustain cleaning while other components may sustain disinfection or sterilization. For example, an ultrasound probe that may be in contact with a patient (e.g., the patient's skin) may undergo high level disinfection before and after use. In another example, a brake of the ultrasound device may be cleaned monthly or when visibly dirty. In one example, an LCD screen of the ultrasound may undergo high level disinfection less frequently than the ultrasound probe. Appropriate levels of processing for components of the ultrasound device may be listed in a user manual or other reference.

BRIEF DESCRIPTION

In one embodiment, a method for conveying information about processing levels for components of an ultrasound device includes displaying the ultrasound device having a first component with a first visual indicator to indicate a first processing level and a second component with a second visual indicator to indicate a second processing level. The first and the second visual indicators may be permanent visually detectable indicators (VDIs) that convey information about cleaning, disinfection, and sterilization (CDS), also herein referred to as processing, of touchable components on the ultrasound device. In the present disclosure, "components" may refer to individual components of the ultrasound device or a distinct group of components. VDIs may also inform users of which components of the ultrasound device may be touched during use of the ultrasound device. VDIs indicate an appropriate degree of processing for different components of the ultrasound device, where the degrees of processing may be based on a use frequency of a component and a surface material of the component.

VDIs implemented on components of the ultrasound device may include, for example, color coding, patterns, e.g., stripes, checkerboard, and so on, and visually different materials on the surface of components, e.g., glass, plastic, metal, and so on. For the color coding, patterns, and different materials, VDIs may completely cover the surface of the components in one example, or only partially cover the surface of the components e.g., a border along the edge of the component or a small or large tag on the surface of the component.

In one example, a VDI may be used for each component of the ultrasound device to indicate an appropriate level of processing for the respective component, where different components of the ultrasound device have different appropriate levels of processing. Alternatively, multiple components may have the same VDI, indicating components with the same VDI may be processed to the same level. Different types of VDIs (e.g., colors, patterns, borders, and so on) may be used on different components to indicate processing levels of the components while adhering to a manufacturer's aesthetic or brand guidelines.

VDIs may be permanent, such that a VDI of a component remains consistent (e.g., the same color, pattern, or material) before, during, and after processing of the component.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1A:
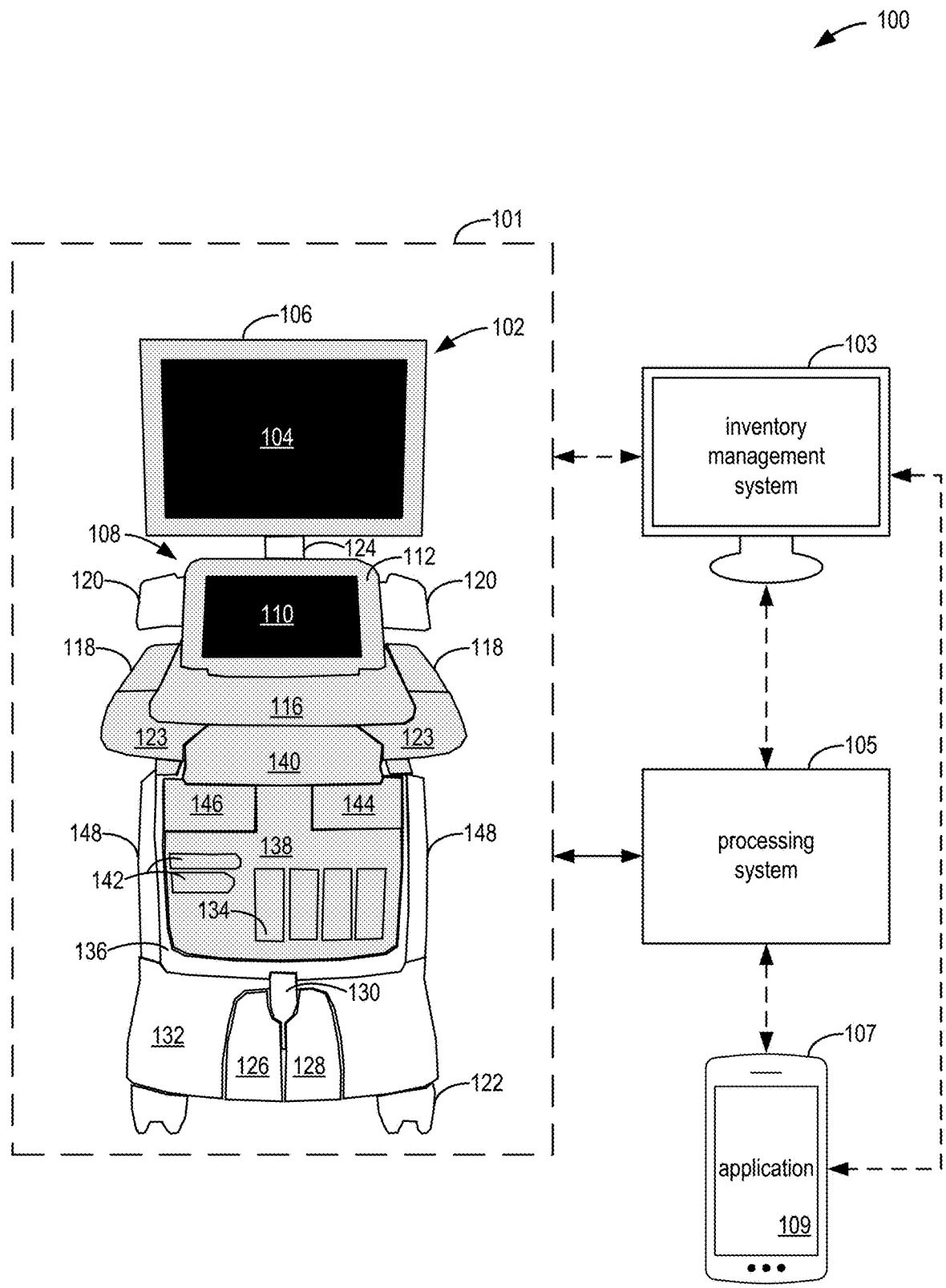
FIG. 1A shows a first example of an ultrasound imaging system in communication with an inventory management system and a processing system.

The following description relates to various embodiments of an ultrasound imaging system with components of the ultrasound imaging system permanently configured with visually detectable indicators (VDIs) used to convey information about processing levels for different components. FIGS. 1A-1D show a schematic diagram of an ultrasound imaging system comprising components configured with VDIs. FIG. 1A also shows an inventory management system (IMS) and a processing system in communication with the ultrasound imaging system. The IMS may maintain a record of medical device conditions, for example, requests for processing of the ultrasound imaging device based on a duration since a last processing event. The processing system may be a human user or an automated processing machine (e.g., robot) which determines a processing level of ultrasound imaging system components based on component VDIs, and process the components.

Figure 1B:
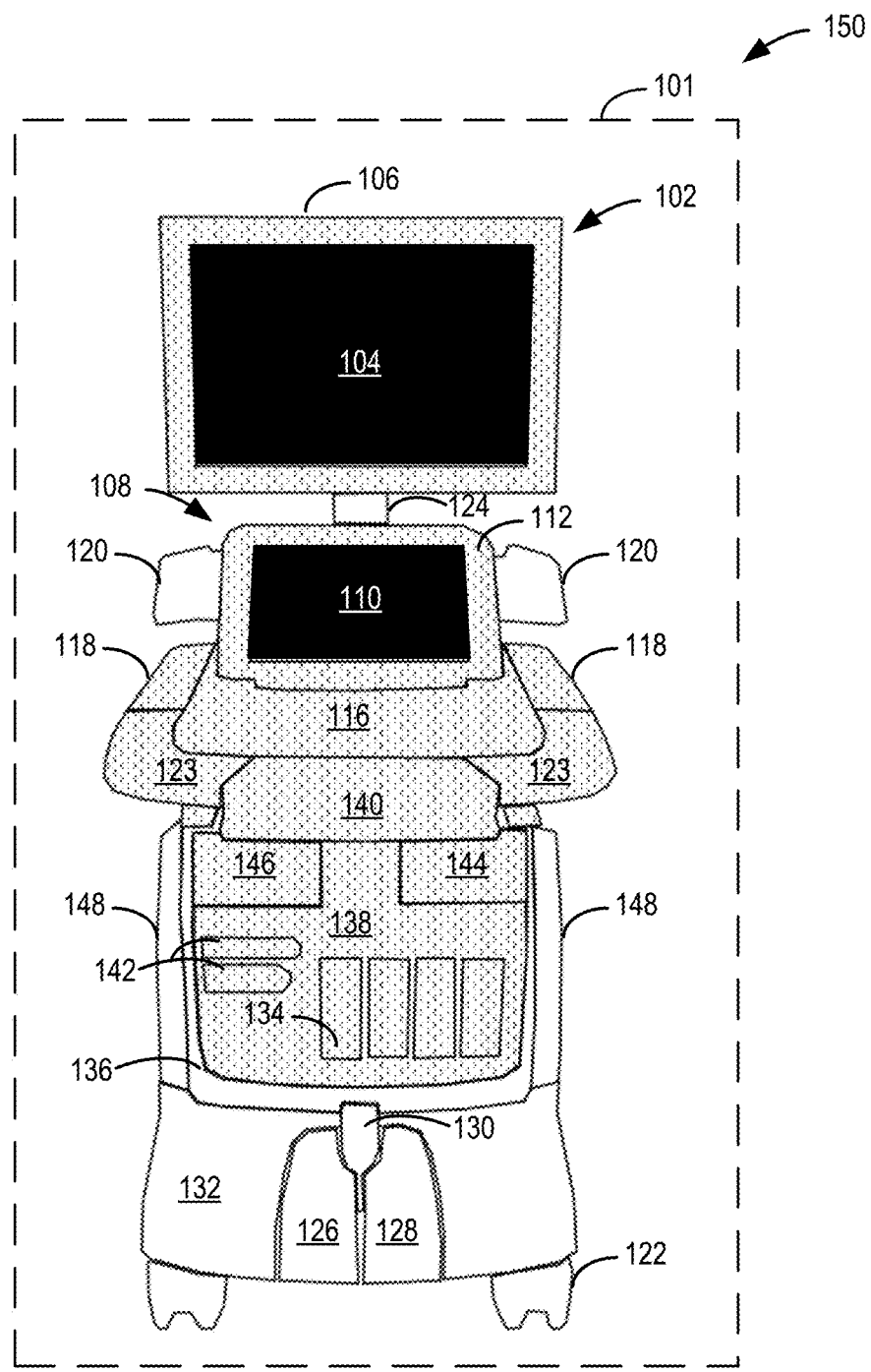
FIG. 1B shows a second example of the ultrasound imaging system of FIG. 1A.
Figure 1C:
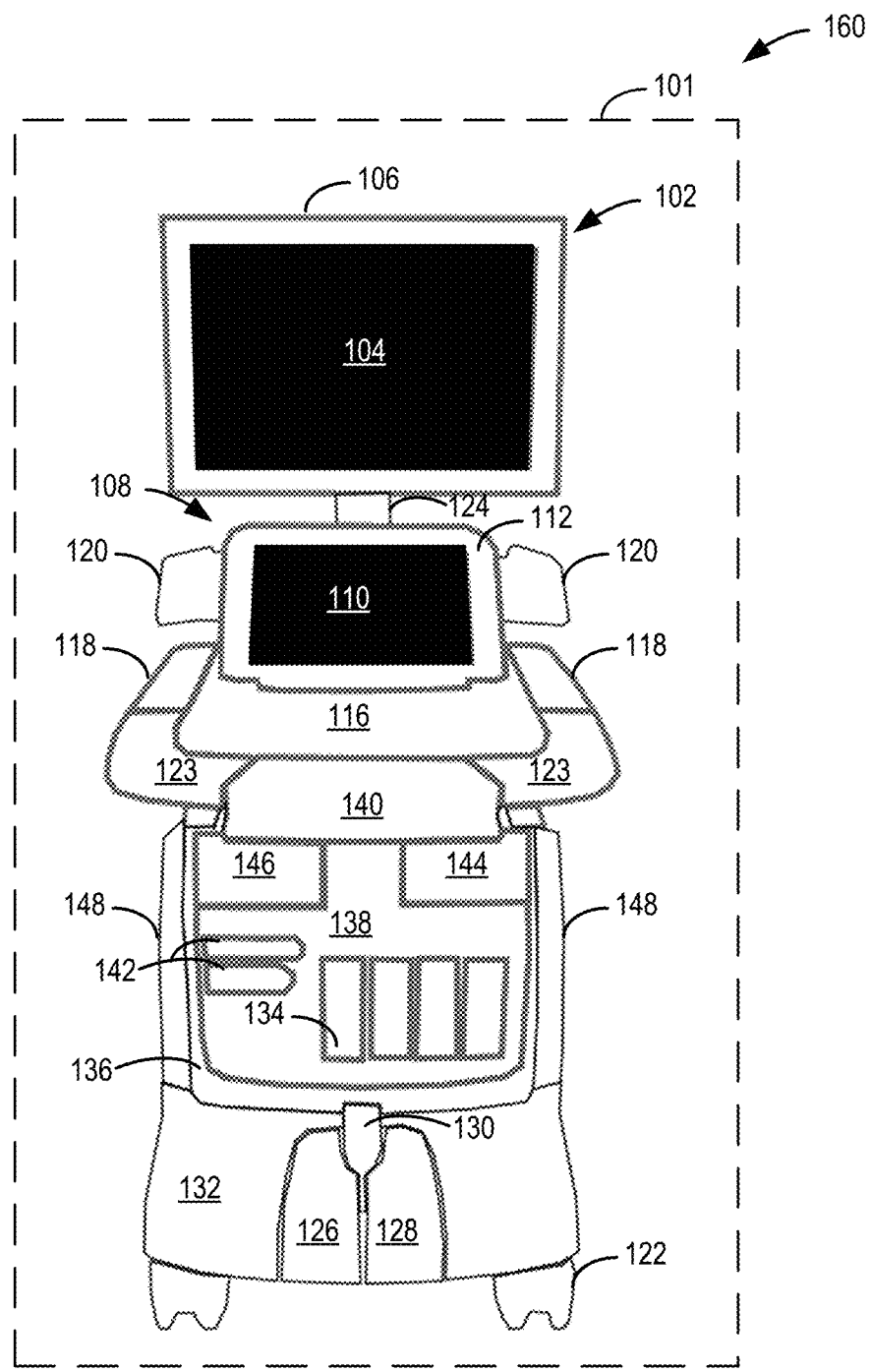
FIG. 1C shows a third example of the ultrasound imaging system of FIG. 1A.

FIG. 1A shows an example of the ultrasound imaging system where VDIs are different colors on the surface of components of the ultrasound imaging system. Though indicated as colors in the example of FIG. 1A, VDIs may further include patterns (as shown in FIG. 1B), materials, borders (as shown in FIG. 1C), and tags (as shown in FIG. 1C), each of which may be used to indicate a level of processing for a respective component of the ultrasound imaging device. Further, an ultrasound imaging system may use combinations of visual indicators such as colors, patterns, materials, borders, and/or tags, in some embodiments.

Figure 2:
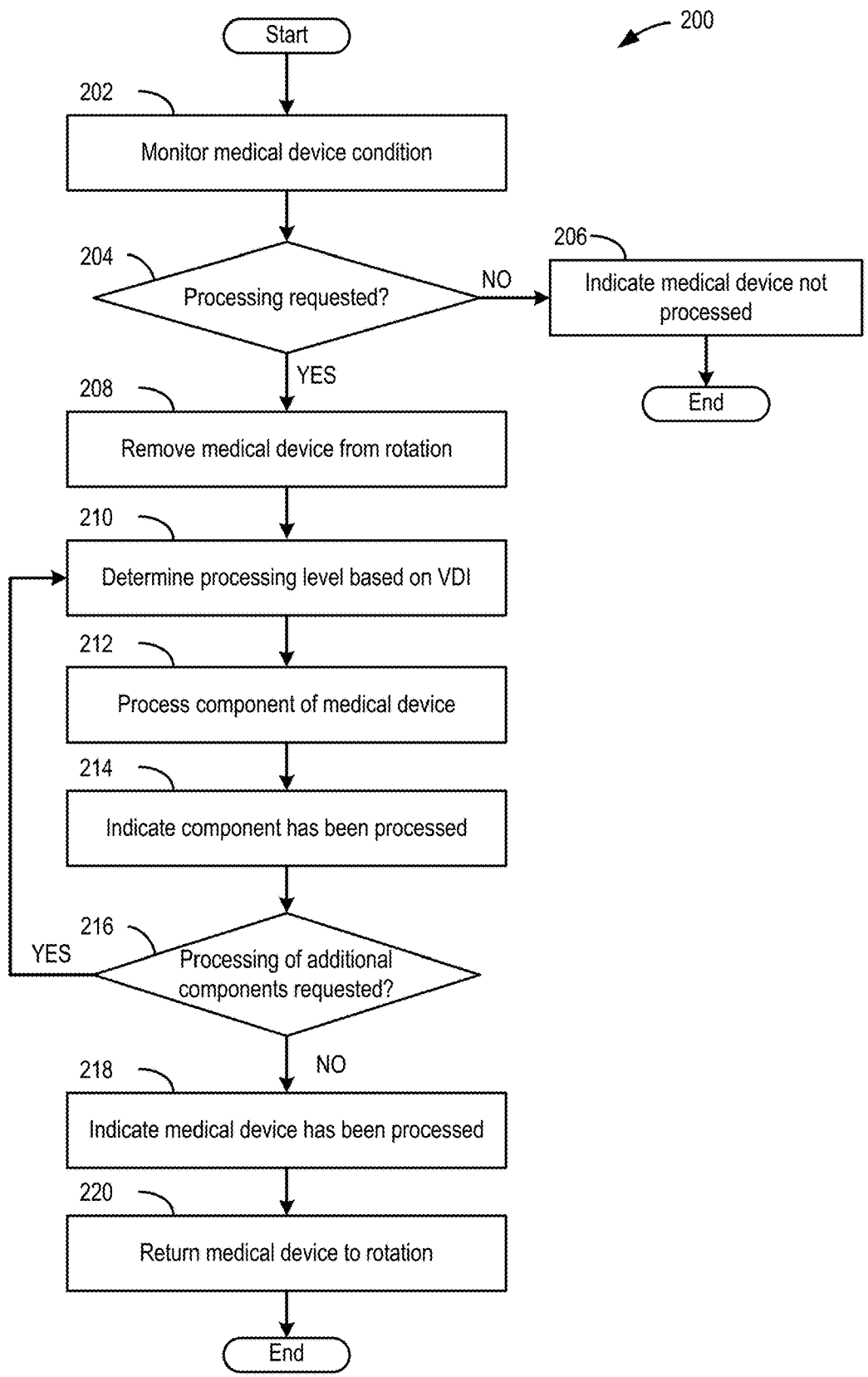
FIG. 2 shows a first example method for processing the ultrasound imaging system of FIGS. 1A-D.
Figure 3A:
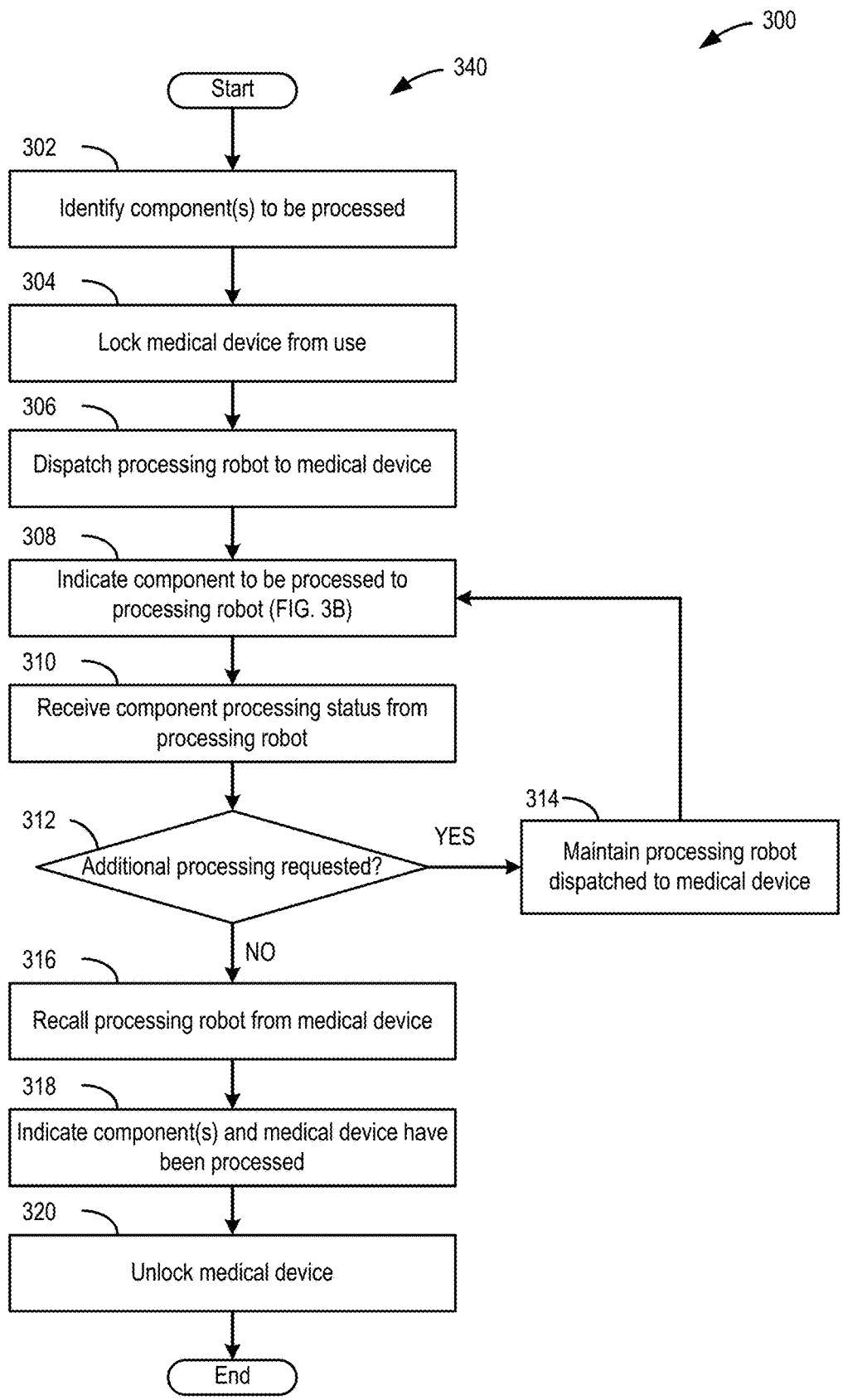
FIGS. 3A-3B shows a second example method for processing the ultrasound imaging system of FIGS. 1A-D.
Figure 3B:
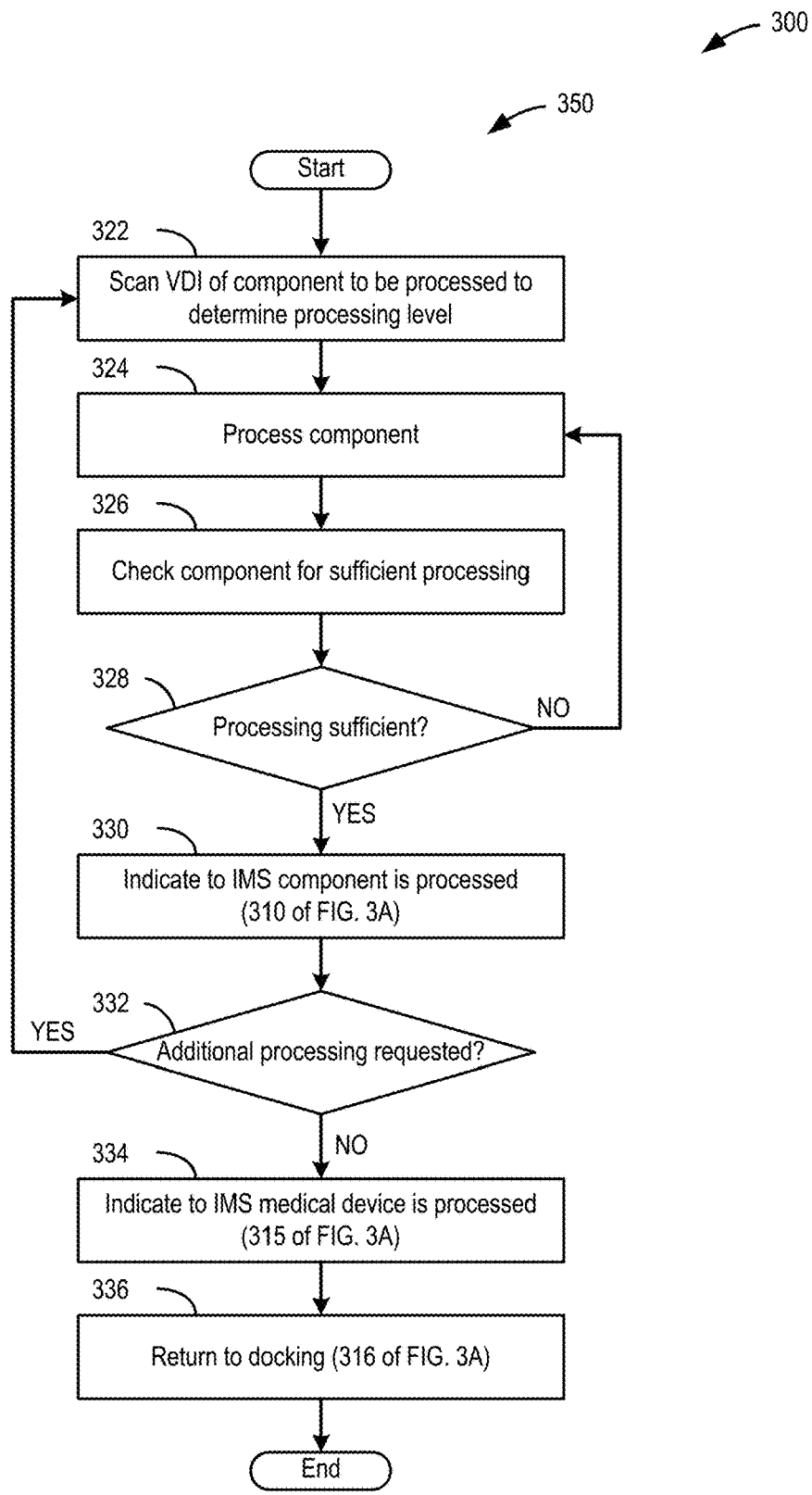
Figure 4:
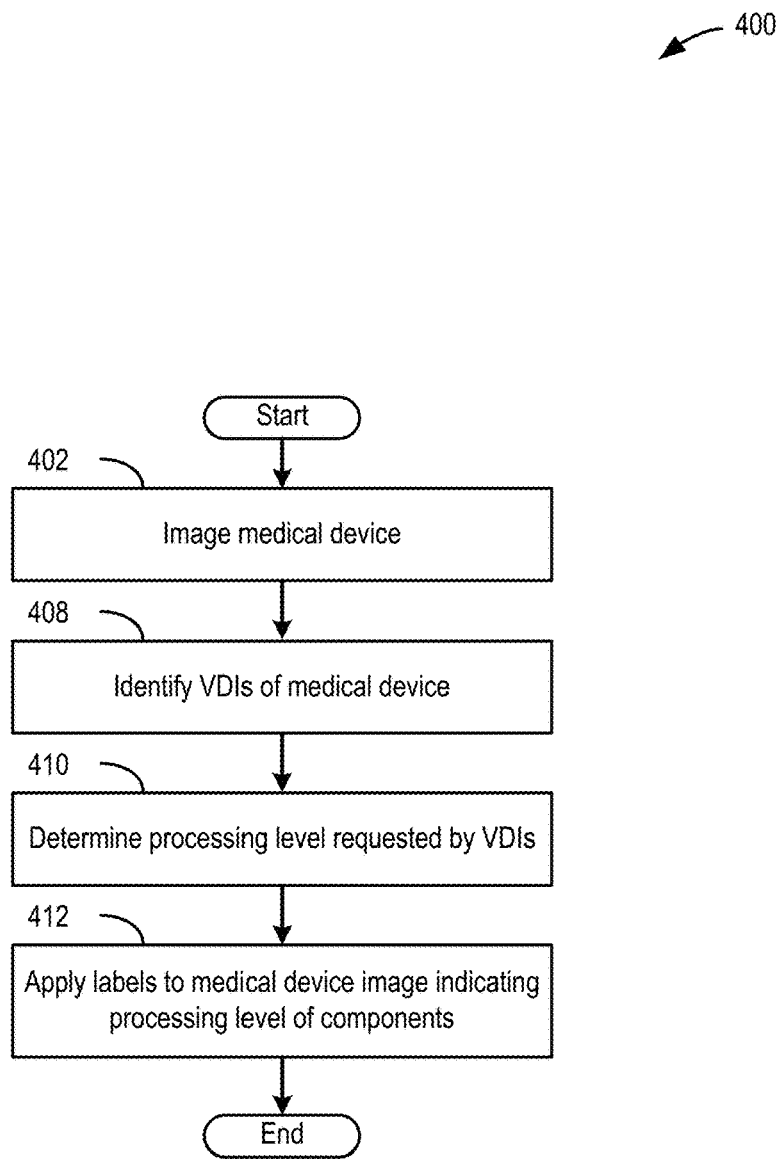
FIG. 4 shows a third example method for processing the ultrasound imaging system of FIGS. 1A-D.

The description also includes a first example method for processing the ultrasound imaging system based on VDIs of ultrasound imaging system components, as shown in FIG. 2. FIGS. 3A-3B elaborate on the method of FIG. 2 and describe a second example method for processing the ultrasound imaging system based on VDIs using the IMS and the processing system, where the processing system is an automated robot. FIG. 4, also elaborating on the method of FIG. 2, describes a third example method for processing the ultrasound imaging system based on VDIs using the IMS and the processing system, where the processing system is a user using a smartphone application.

Turning now to the figures, FIG. 1A illustrates an example medical device 101 according to one embodiment. In the illustrated embodiment, the medical device 101 is an ultrasound imaging system 101. However, it may be understood that embodiments set forth herein may be implemented using other types of medical imaging modalities (e.g., MRI, CT, PET/CT, and so on). As shown, the ultrasound imaging system 101 includes multiple components. The components may be coupled to one another to form a single structure, for example, a unitary system that is capable of being moved (e.g., portably) from room to room. For example, the ultrasound imaging system 101 may include wheels 122, as in the present illustration, or be transported on a cart, in another example. Further, the ultrasound imaging system 101 may include handles 123 where the system 101 may be grasped by a user to move the system 101. For embodiments of the system 101 configured with wheels 122, the system 101 may be configured with a left brake pedal 126, a right brake pedal 128, and a middle brake pedal 130. The left, right, and middle brake pedals 126, 128, 130 are positioned on a front side of the system 101 and in the center of a front bumper 132. The system 101 may be raised or lowered, for example, in a direction parallel with gravity, using an up/down controls 140. The front side of the system 101 further includes a front panel 136, a front cover 138, side panels 148, network and hard disk drive indicators 142, a CD/DVD disk drive 144, and a black and white printer 146.

The ultrasound imaging system 101 includes a transmit beamformer and a transmitter that drives elements (e.g., transducer elements) within a transducer array, herein referred to as a probe (not shown) to emit pulsed ultrasonic signals (referred to herein as transmit pulses) into a body (not shown). According to an embodiment, the probe may be a one-dimensional transducer array probe. However, in some embodiments, the probe may be a two-dimensional matrix transducer array probe. As explained further below, the transducer elements may be comprised of a piezoelectric material. When a voltage is applied to a piezoelectric crystal, the crystal physically expands and contracts, emitting an ultrasonic spherical wave. In this way, transducer elements may convert electronic transmit signals into acoustic transmit beams. The ultrasonic signals are back-scattered from structures in the body, for example, blood vessels and surrounding tissue, to produce echoes that return to the probe and are processed by the ultrasound imaging system to produce data representative of the echo signals.

The ultrasound imaging system 101 includes a plurality of probes (not shown) that may be stored in a probe holder 118. For example, each of the plurality of probes may be assigned to a specific position (or probe slot) within the probe holder 118, which may be programmed in a system controller of the ultrasound imaging system 101. Further, the probe type of each probe of the plurality of probes may be programmed in the system controller. For example, the plurality of probes may include a curvilinear probe that is assigned to be stored in a first position of the probe holder 118, a different type of curvilinear probe that is assigned to be stored in a second position of the probe holder 118, a linear probe that is assigned to be stored in a third position of the probe holder 118, and a phased array probe that is assigned to be stored in a fourth position of the probe holder 118. The ultrasound imaging system 101 may also include an upper holder 120, which may be a gel warmer in one example and may be a specialty probe holder in a second example. The plurality of probes may be coupled to the system 101 at probe connectors 134, positioned on the front cover 138 of the system 101.

The system 101 further includes a user interface that enables an operator to control at least some of the operations of the system 101. The user interface may include hardware, firmware, software, or a combination thereof that enables the operator (e.g., user) to directly or indirectly control operation of the system 101 and the various components thereof. As shown, the user interface includes a first display device 102 having a first display area 104 and a first frame 106, and a second display device 108 having a second display area 110 and a second frame 112. In one example, the first and the second display devices 102, 108 are LCD monitors. The first display device 102 may be coupled to a body of the system 101 by an adjustable arm 124.

In some embodiments, the user interface may also include one or more user interface input device 116, such as a physical keyboard, mouse, and/or touchpad. In one embodiment, the second display device 108 is configured as a touchpad such that when a user moves a finger/glove/stylus across the second display area 110 of the touchpad, a cursor atop the ultrasound image on the first display area 104 moves in a corresponding manner. In another embodiment, the first display device 102 and/or the second display device 108 are touch-sensitive displays (e.g., touchscreen) that can detect a presence of a touch from the operator on the first and the second display areas 104, 110 and can also identify a location of the touch on the first and the second display areas 104, 110. The touch may be applied by, for example, at least one of an individual's hand, glove, stylus, or the like. As such, the touch-sensitive display may also be characterized as an input device that is configured to receive inputs from the operator. The first and the second display devices 102, 108 also communicate information from the controller to the operator by displaying the information to the operator. The first and the second display devices 102, 108 and/or the user interface input device 116 may also communicate audibly. The first and the second display devices 102, 108 are configured to present information to the operator during the imaging session. The information presented may include ultrasound images, graphical elements, user-selectable elements, and other information (e.g., administrative information, personal information of the patient, and the like).

During operation, the ultrasound imaging system 101 may acquire data, for example, volumetric data sets, by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound images of the system 101 may be generated from the acquired data (at the controller) and displayed to the operator or user on the first and the second display devices 102, 108. A graphics module and an image analysis module, among other potential modules of an ultrasound image processing module, may coordinate with one another to present information to the operator during and/or after the imaging session. For example, the graphics module may be configured to display designated graphics along with the ultrasound image on the first and the second display devices 102, 108, such as graphical outlines that represent lumens or vessel walls in the acquired image. The graphics module and/or image analysis module within the ultrasound image processing module of the controller may also be configured to generate a 3D rendering or image (not shown) of an imaged structure.

In various embodiments of the present disclosure, one or more components of ultrasound imaging system 101 may be included in a portable, handheld ultrasound imaging device. For example, the first and the second display devices 102, 108 and user interface input device 116 may be integrated into an exterior surface of the handheld ultrasound imaging device, which may further contain a processor and memory. The probe may comprise a handheld probe in electronic communication with the handheld ultrasound imaging device to collect raw ultrasound data. The transmit beamformer, transmitter, receiver, and receive beamformer may be included in the same or different portions of the ultrasound imaging system 101. For example, the transmit beamformer, transmitter, receiver, and receive beamformer may be included in the handheld ultrasound imaging device, the probe, and combinations thereof.

The ultrasound imaging system 101 may include a number of components which may each have a different level of processing applied thereto for cleaning, disinfecting, or sanitizing a component. Different components of the system may use different levels of processing to achieve an appropriate level of cleanliness (e.g., below a non-zero, positive threshold of contamination) for the component. The appropriate level of cleanliness for a component may be determined based on a surface material of the component, a use of the component, and/or a use frequency of the component. A different processing agent may be used for components formed of metal compared to components formed of plastic, in one example. Further, components may contain paint applied thereto which may be degraded by certain processing agents. Regarding component use and use frequency, a component that is touched by a user's foot, for example, the left brake pedal 126, the right brake pedal 128, the middle brake pedal 130, may be cleaned less often (e.g., monthly) and to a lower processing level (e.g., cleaned) than a component that comes in contact with a patient, for example, the probe, which may be processed at a higher level (e.g., disinfected) more often (e.g., before and after each patient).

Processing agents may include, but are not limited to, 70% isopropyl alcohol, Distel High-Level Disinfectant Wipes, Clinell Clorox Wipes, Clinell Universal Sanitizing Wipes, Septiwipes, and 5.25% Sodium Hypochlorite (Bleach). Additional processing agents may include common soap and water for low level processing (e.g., cleaning) and ultraviolet rays (UV) for high level processing (e.g., disinfecting and sanitizing).

As different components of system 101 may have different appropriate levels of processing based on component use, use frequency, and surface material, and given system 101 may include many components, a user may refer to an external reference, such as a user manual, to determine an appropriate processing level for each components. However, referring to an external reference to determine the appropriate processing level for each component may take time that a healthcare provider may instead be using to treat a patient, for example. To reduce an amount of time spent determining appropriate processing levels for components and processing the components, a user may disinfect all surfaces of the system 101. However, if an incorrect processing method is applied to a component of the system, the component may be damaged, and restoring function of the component may include repairing or replacing the component. In another example, damage to the component may render the system inoperable. Additionally, applying a low level of processing where a high level of processing is used to clean the component to a desired level may result in insufficient processing (e.g., cleaning instead of sterilization), which may result in patient or user contamination. In another example, using a high level processing method on components which use a low level processing method (e.g., sterilizing wheels 122) may result in excess time spent by a user to process the system, as well as greater processing cost, which may result from processing agents and labor costs.

A system and method are thus desired for reducing a time, cost, and complexity of conventional methods for processing medical devices, such as an ultrasound imaging system. The present disclosure describes a method for conveying information about processing levels for components of an ultrasound device, including displaying the ultrasound device having a first component with a first visual indicator to indicate a first processing level and a second component with a second visual indicator to indicate a second processing level.

The first component and the second component may each be a single component of the system, for example, the first component may be the user interface input device 116 and the second component may be the left brake pedal 126. Each of the first component and the second component may be configured with a VDI to indicate a processing level for the component. As the system 101 has more than two touchable components, the system may be configured with a third component, a fourth component, and so on.

In another example, components of the ultrasound imaging system 101 may be grouped by their function. For example, a screen group of the system may include the first display device 102 and the second display device 108. A tool group of the system 101 may include the first frame 106, the second frame 112, the user interface input device 116, the probe holder 118, the handles 123, the probe connectors 134, the front cover 138, the up/down controls 140, the network and hard disk drive indicators 142, the CD/DVD disk drive 144, and the black and white printer 146. A body group of the system 101 may include remaining components of the system 101, including the upper holder 120, wheels 122, the adjustable arm 124, the left brake pedal 126, the right brake pedal 128, the middle brake pedal 130, the front bumper 132, the front panel 136, and side panels 148. In this example, the first component may be the body group and the second component may be the tools group.

The first visual indicator and the second visual indicators may each be a VDI of the respective component indicating the appropriate processing level for the respective component. VDIs may be, for example, color coding, patterns, materials, and so on covering at least part of a surface of the respective component. As there may be more than two processing levels, there may be more than two VDIs. In one example, a VDI of the first component may be a different color, pattern, or material than a VDI of the second component to indicate an appropriate level of processing for each of the first component and the second component. Each component of the system 101 may have a VDI to convey information regarding an appropriate processing level for the component, where different components of the ultrasound device may have different appropriate levels of processing. The ultrasound imaging system may thus comprise a number of components, each with a respective VDI indicating an appropriate processing level for respective surfaces of the respective components.

VDIs may be permanent, such that a VDI of a component remains consistent (e.g., the same color, pattern, or material) before, during, and after processing of the component. When displayed as colors, patterns, and materials, VDIs may completely cover the surface of the respective component in one example, or only partially cover the surface of the respective component e.g., a border along the edge of the component or a small or large tag on the component.

Processing levels indicated by VDIs may be one of five distinct processing levels, including cleaning, low level disinfection, intermediate level disinfection, high level disinfection, and sterilization. Sterilization may be used for probes that penetrate the body and enter the bloodstream, and so on. High level disinfection may be used for probes that contact mucous membranes. Intermediate level disinfection may be used for external probes that touch intact skin. Low level disinfection may be used for parts that have indirect patient contact where the user touches both the patient and these parts, for example, the user interface, handles, probe holders, cable hooks, monitor, and so on. Cleaning may be used for parts that are unlikely to have indirect patient contact, e.g., parts the user doesn't touch with their hands when scanning a patient. These may include wheels, backside of the scanner, speakers, foot pedals, and so on. In one example, the five processing levels may be depicted using five distinct VDIs or more than five VDIs where each VDI may be at least one of five different colors, five different patterns, five different materials, and so on. More than one component may have a VDI indicating the same processing level such that more than one component may be processed to the same processing level, as further described below.

VDIs may be read and interpreted by a processing system 105, which may be in wireless communication with the ultrasound imaging system 101. Based on interpretation of VDIs, the processing system 105 may process a component or components of the ultrasound imaging system 101 to a processing level indicated by the VDI.

In a first example, the processing system 105 may be a robot in wireless communication with an IMS 103. The IMS 103 may control (e.g., remotely operate) the robot, for example, directing the robot to identify, via an image processing system, contaminated components of the ultrasound imaging system 101 and process, via a processing apparatus, a contaminated component in accordance with a processing level indicated by a VDI of the contaminated component. The image processing system may include one or more cameras and instructions stored in memory to process images of the ultrasound imaging system 101 and segment the image to identify processing levels for various components based on the VDI of the different components. The processing apparatus may include a moveable arm configured with nozzles for applying a processing agent to the system 101 and a gripping mechanism for holding a disinfecting wipe or other processing agent, in one example. The IMS 103 may further be in wireless or wired communication with the ultrasound imaging system 101. For example, the IMS 103 may monitor a condition of the ultrasound imaging system 101, such as a duration since a prior processing event, and may lock the system 101 from use until the system 101 has been processed, for example, by the processing system 105 robot. Further details regarding the processing system 105 as a robot in communication with the IMS 103 are described in FIGS. 3A-3B.

In a second example, the processing system 105 may be a user, such as a medical provider, janitor, maintenance worker, and so on. The user may use a handheld imaging system 107 configured with an application 109 for reading and interpreting VDIs of the ultrasound imaging system 101. In the example of FIG. 1A, the handheld imaging system 107 is a smartphone, however in other examples, the handheld imaging system 107 may be a tablet or other handheld technology with a camera and image processing capabilities, as further described below. The user may then process components of the ultrasound imaging system 101 to processing levels indicated by the application 109. The smartphone 107 may further be in wireless communication with the IMS 103 to indicate a processing status of the ultrasound imaging system 101. Further details regarding the processing system 105 as a user with the smartphone 107 and application 109 are described in FIG. 4.

As briefly described above, the ultrasound imaging system 101 may be configured with different types of VDIs, including color coding, patterns, borders, and tags to indicate processing levels for components of the system. FIG. 1A shows a first example type of VDI 100, where processing levels may be indicated by different colored components. For example, the left brake pedal 126 VDI may be a white color covering the surface of the left brake pedal. The white color may indicate a low processing level (e.g., cleaning). The user interface input device 116 VDI may be a grey color covering the surface of the user interface input devices. The grey color may indicate a medium processing level (e.g., low level disinfection, intermediate level disinfection, or high level disinfection). The second display device 108 VDI may be a grey color of the second frame 112 of the second display area 110.

As described above, components of the ultrasound imaging system 101 may be grouped based on use or use frequency. For example, the tool group and the body group may each have different VDIs, where the tool group VDI is a grey color and the body group VDI is a white color. The screen group may have a VDI type other than color, as further described below. Each VDI may indicate a level of processing for all components of the respective group, as all components of the group may by the same color.

Alternatively, components with the same or similar uses and/or use frequencies may have different VDIs regardless of grouping. For example, the user interface input device 116 and the handles 123 may both be touched regularly by a user (e.g., a medical provider), and thus be considered to be in the tools group. However, the user interface input device 116 may be touched more frequently (e.g., multiple times during a patient exam) than the handles 123 (e.g., when moving the system 101 to a new patient). In this example, the handles 123 VDI may be different from the user interface input device 116 VDI. For example, the handles 123 VDI may be a green color, which may indicate low level disinfection and the user interface input device 116 VDI may be a blue color, which may indicate high level disinfection.

As briefly described above, VDIs may also be patterns covering a surface of components of the ultrasound imaging system 101. As shown in FIG. 1B, the ultrasound imaging system 101 may have a second example type of VDI 150, where the tools group VDI may be a first pattern covering surfaces of components in the tools group and the body group VDI may be a lack of pattern covering surfaces of components in the body group. In another example, the body group VDI may be a second pattern (e.g., dots) that is different from the first pattern (e.g., stripes) of the tools group VDI. Additionally, individual components within the same group may have different VDIs comprised of different patterns indicating different processing levels. For example, the up/down controls 140 may be touched more frequently than the CD/DVD disk drive 144, therefore the up/down controls 140 VDI may be a third pattern indicating high level disinfection and the CD/DVD disk drive 144 VDI may be a fourth pattern indicating low level disinfection.

FIG. 1C shows a third example type of VDI 160, where VDIs may be a border (e.g., a line of color and/or material) around an outer edge of the component different from the color and/or material of the component. For example, the up/down controls VDI may be a grey border is painted around an outer edge of the up/down controls 140 and the front bumper VDI may be no border painted around an outer edge of the front bumper 132. In another example, the front bumper VDI may be a second border, for example, a different color, material, or thickness than the up/down controls VDI. Additionally, components within the same group may have the same VDI with a single border around components along an edge of the group, for example, the tools group VDI may include a border along edges of the front cover 138 and might not include a border along edges of the probe connectors 134. Alternatively, components within the same group may each have different VDIs comprised of different borders indicating an appropriate processing level for each component.

Figure 1D:
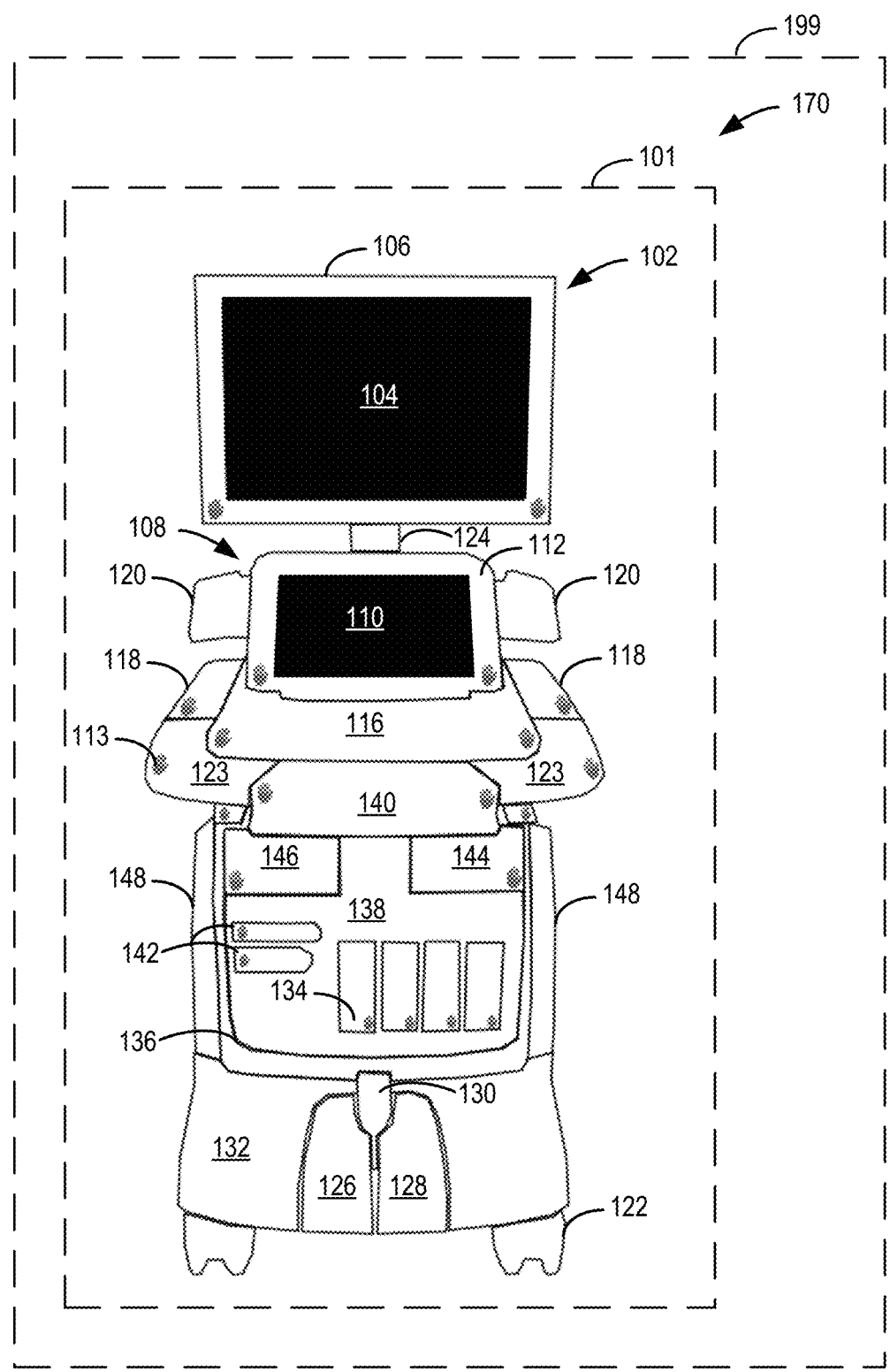
FIG. 1D shows a fourth example of the ultrasound imaging system of FIG. 1A.

A fourth example type of VDI 170 are shown by FIG. 1D, where VDIs may be a tag 113 on a surface of a component of the ultrasound imaging system 101. Also in this example, the ultrasound imaging system 101, including at least one tag 113, may be displayed on an image rendering device 199, as opposed to FIGS. 1A-1C which illustrate a physical manifestation of the medical device. For example, the image rendering device 199 may be a display device of the inventory management system 103, a display device of the processing system 105 when configured as a robot, or a display device of the smartphone 107. The image rendering device may provide augmented reality overlays over displayed images captured and processed by a camera coupled with the image rendering device. In an example, the overlay may include the VDI elements at appropriate locations in the pictorial display even though the VDI elements are not present on the physical device being imaged (and displayed). For example, the system may provide an augmented reality view of the physical medical device with an overlay of the VDIs on the screen at the appropriate screen locations determined from image segmentation to correspond to the surfaces and indicate the appropriate level of processing. The image segmentation may identify the components and display an outline of the various components overlaid on the displayed image of the device, thus augmenting the image. Further, within the outline, the system may provide processing levels (e.g., numbers as one example) based on querying a database that provides a correlation of the processing level of particularly identified components. In this way, the augmented displayed image may indicate to a user the requested processing levels of the different components directly on the display of the components.

A technical challenge in the use of augmented reality overlays in real-time is that depending on the particular device being imaged and current conditions as determined by the inventory management system, the particular components may be set for different levels of processing. For example, during a particular pandemic condition, various components may be set to a higher level of processing, as compared to non-pandemic conditions. Additionally, the same component of the device may have different set levels of processing depending on the inventory plan for the device, for example if the device is planned for storage, or shipment, etc. As such, the current conditions can affect the processing level to be provided on the augmented reality overlay, and those conditions can change in real-time. However, by utilizing a database as noted above in the inventory management system, for example, in combination with image segmentation in real-time, the image rendering device is able to display an up-to-date processing level based on the updated information in the database by the management system, even when the ultrasound device may move around a facility and be used by a variety of users for a variety of purposes. This approach enables more efficient processing as the database can be grouped by individual device ID as well as current facility conditions and updated by the inventory management system in real-time, and then used in real-time via the overlay.

The tag 113 may be a symbol, a shape, or a colored tag indicating a processing level. For example, the system 101 may have a tools group VDI on components of the tools group, where the tools group VDI is the tag 113. In one example, the tag 113 may be a hand, indicating components with the tools group VDI may be touched by a hand of a user. Components of the body group and the screen group VDI may be the lack of the tag 113.

In another example, VDIs may indicate a processing level of the respective component. For example, a tag may be a spray bottle to indicate disinfection, a hand to indicate cleaning, and a sun to indicate sanitization using UV. Components within the same group may have the same VDI with a small tag on each component of the group, or may have different VDIs comprised of tags indicating different processing levels.

For components that might not be able to be labeled with a VDI as described above (e.g., color, pattern, border, tag), a VDI may be a material of the component itself. For example, when the first display device 102 and the second display device 108 are touch screens, the LCD screen (e.g., the touch screen material) may be the touch screens VDI. The touch screens VDI may indicate a medium processing level (e.g., low level disinfection, intermediate level disinfection, or high level disinfection), which may be a same processing level or a different processing level relative to processing level of other components of the ultrasound imaging system 101 as indicated by respective component VDIs.

A component of the ultrasound imaging system 101 may be configured with multiple VDIs to indicate whether the component may be touched by a user as well as a processing level of the component. For example, the user interface input device 116 may have a blue color over the surface of the user interface input devices indicating high level disinfection (e.g., a first VDI), and a hand symbol tag, indicating the user interface input devices may be touched by a user (e.g., a second VDI). In the same example, the handles 123 may have a green color over the surface of the handles indicating low level disinfection (e.g., a third VDI), and a hand symbol tag, indicating the user interface input devices may be touched by a user (e.g., a fourth VDI).

In another example, processing levels for components of the system 101 may be depicted using a combination of different VDIs (e.g., colors, patterns, borders, materials, tags, and so on). For example, the front bumper 132 VDI may be a color, the up/down controls 140 VDI may be a border, and the handles 123 VDI may be a tag. Using a combination of colors, patterns, borders, materials, tags, and so on for VDIs may allow for indication of processing levels for components while adhering to a manufacturer's aesthetic or brand guidelines. As another example, the user interface input device 116 VDI may be a checkerboard pattern, the user interface input device may be formed of plastic, or a hand symbol tag placed thereon. In the same example, the handles 123 VDI may be a striped pattern, the handles may be formed of metal, or a spray bottle tag may be placed thereon. The left brake pedal 126 VDI may be a dotted pattern, the left brake pedal being formed of a textured plastic, or no tag placed thereon.

Example VDIs described in FIGS. 1A-1D may be non-limiting examples of VDIs used to indicate processing levels for components of medical devices. VDIs may be any marking, symbol, or other indicator that may inform a user or other system used to process the ultrasound imaging system of appropriate processing levels for each component of the ultrasound imaging system. Further details regarding detection and interpretation of VDIs, as well as processing of ultrasound imaging system components are described in FIGS. 2-4.

Configuring the ultrasound imaging system 101 with permanent VDIs used to convey information about a level of processing for a component of the system configured with a VDI may clearly indicate a level of processing used for the component, which may allow users processing the system to quickly identify components to be processed and the appropriate level of processing. This may reduce time and costs associated with processing more components than is requested based on contamination or duration since prior processing, or costs and time associated with processing components at a higher level than is requested. Additionally, the system may result in efficient processing of components, which may reduce contamination of both a patient and a user. VDIs may allow for safer use of the ultrasound imaging device by a user and for a patient which the device is being used on, as indication of which components of the ultrasound device might or might not be touched may reduce instances of component or patient contamination due to touching of a component that might have undergone an insufficient level of processing.

FIG. 2 shows an example high-level method 200 for processing a medical device based on component VDIs. For example, a component VDI may communicate a level of processing for the component based on VDI color, material, pattern, border, tag, and so on. Method 200 is described in reference to the ultrasound imaging system 101 of FIGS. 1A-1D, and may be applied to other medical devices configured with VDIs as described above. Method 200 may be conducted by a processing system, which may be a medical personnel, a janitor, maintenance staff, a robot, and so on. The processing system may be in communication with an IMS and use a smartphone application or other tools to process the medical device. Further examples describing use of the IMS and a robot are described in FIGS. 3A-3B and use of a smartphone application by a user are described in FIG. 4.

At 202, method 200 includes monitoring the medical device condition, which may include determining a duration since a last processing event of the medical device or components thereof. In one example, determining the duration since the last processing event may include the IMS referring to a memory of the IMS, which may store a time/date of the last processing event. Monitoring the medical device condition may also include determining a contamination level of components, for example, by shining a UV light over the surface of the components to detect bacterial contamination. Further medical device conditions to be monitored may include determining a duration since last use of the device, or if the device is about to be used.

At 204, method 200 includes determining if processing has been requested. In one example, processing may be requested based on a contamination level of a component being greater than a non-zero, positive contamination threshold, a duration since the last processing event being greater than a non-zero, positive threshold duration, indication the medical device was previously used or is about to be used, the medical device being powered off, processing being requested by a user, and so on. For example, the contamination threshold may be a percentage of the surface of the component above which patient or user contamination may result in infection. The threshold duration may be, in one example, two hours since a prior processing event. If it is determined that processing is not requested at 204, at 206, method 200 includes indicating the medical device has not been processed and method 200 ends. In one example, the medical device may be used with low risk of patient or user contamination as components that have not been processed might not be in contact with the patient or user during use of the medical device, for example a brake pedal. In another example, processing might not be requested as the medical device may be determined to be sufficiently processed e.g., components may have multiple uses allowed between processing.

If at 204 it is determined processing is requested, at 208, method 200 includes removing the medical device from rotation. This may include powering off the device, indicating that the device is not to be used (e.g., by displaying a sign on the device), physically removing the device from proximity to a patient (e.g., from a patient's room), using the IMS to lock the device from being used, and so on.

At 210, method 200 includes determining a processing level for a first component of the medical device to be processed based on the first component VDI. The processing level may be determined by a processing system (e.g., a user or a robot). In one example, the user may use a smartphone application to scan the first component VDI and the application may inform the user of what processing level is indicated by the VDI. In another example, the robot used to process the medical device may scan the component VDI and information about the corresponding processing level may be stored in memory of the robot. For example, a green color on the first component may indicate intermediate level disinfection as the appropriate processing level for the first component.

At 212, method 200 includes processing the first component of the medical device. The first component may be processed by the processing system according to a method corresponding to the processing level indicated by the first component VDI at 210. Processing may include applying processing agent (e.g., a soap, a disinfectant wipe, or a sterilizing source) in accordance with the indicated processing level. A surface of the first component may be processed. A contamination level of the first component may be monitored after processing, as further described in FIGS. 3A-3B and FIG. 4, and the first component may be processed multiple times according to the indicated processing level to achieve a desired cleanliness level (e.g., where contamination is below the contamination threshold).

At 214, method 200 includes indicating the first component has been processed, which may include changing a status of the component in the IMS. For example, the user may press a button on the application which marks the component as processed on the application and generates a signal indicating the component has been processed. In another example, the processing robot may generate a signal indicating the component has been processed. The processing system (e.g., the user or the robot) may transmit the signal to the IMS via wireless communication indicating that the first component has been processed. The IMS may then change the status of the component stored in the memory of the IMS.

At 216, method 200 includes determining if processing of additional components is requested. For example, the IMS may indicate a second component is contaminated or a duration of time greater than the threshold duration of time has passed since the second component was last processed. In another example, the robot may detect contamination greater than the threshold contamination level on the second component of the device. If processing of additional components is requested, method 200 repeats to 210 to determine an appropriate processing level based on the second component VDI and process the second component, according to steps 210-216. Steps 210-216 may be repeated for as many components for which processing is requested.

At 216, if it is indicated that processing of additional components is not requested, at 218, method 200 includes indicating the medical device has been processed. This may include updating a status of the medical device in the IMS to indicate the medical device may be used with a low risk of contamination due to sufficient processing. For example, after some or all components of the medical device have been processed as a result of processing requested at 204 and throughout method 200, the device may be considered to have a contamination level below the contamination threshold and therefore the device may be used by user on a patient with low risk of contamination to the user and or patient.

At 220, method 200 includes returning the medical device to rotation. This may include, for example, if the device was removed from proximity to patient, moving the device in proximity to the patient. In another example, when removing the device from rotation included powering off the device, returning the device to rotation may include powering on the device. Further, if the IMS locked the device from being used, the IMS may remove use restrictions. Method 200 ends.

In this way, component VDIs may be detected and interpreted by a processing system to determine an appropriate processing level for the respective component. Based on a known method associated with a processing level, the processing system may process components of the device for which processing is requested. Different components may have different appropriate processing levels, as indicated by different VDIs. The method of FIG. 2 may be applied using different technologies, as further described in FIGS. 3A-3B and FIG. 4.

FIGS. 3A-3B expand on method 200 of FIG. 2 and describe an example method 300 where processing a medical device based on component VDIs of the medical device includes using an IMS (e.g., the IMS 103 of FIG. 1A) and a robot processing system to detect and interpret VDIs and process device components. FIG. 3A describes a first part 340 of method 300 implemented by the IMS and FIG. 3B describes a second part 350 of method 300 implemented by the robot processing system. The first part 340 and the second part 350 of the method 300, as described respectively in FIGS. 3A-3B, may occur simultaneously and collaboratively. For example, the first part 340 may be performed by the IMS at the same time as the second part 350 is performed by the robot, and steps of the first part 340 performed by the IMS may actuate steps of the second part 350 performed by the robot, as further described below. Method 300 is herein described in respect to one medical device (e.g., the ultrasound imaging system 101) in communication with the robot processing system and the IMS. In other examples, the IMS may be in communication with multiple medical devices and multiple robot processing systems, where multiple instances of method 300 may be run by a single IMS to process multiple medical devices using multiple robot processing systems.

With respect to one medical device, one IMS, and one robot processing system, method 300 may be implemented after each use of the medical device, for example, after the device has been powered off, after a data collection program has been exited, and so on. The IMS may indicate a processing request for the medical device based on a processing frequency of the device and indication the device has been processed. For example, if greater than a threshold duration has elapsed since a prior processing of the device, the IMS may indicate a request for device processing. In another example, device processing may be requested by a user after the device has been used on a patient or prior to device use on a new patient.

Starting with FIG. 3A, at 302, the first part 340 of method 300 includes identifying components of the medical device to be processed using the IMS. A component to be processed may be identified based on a predetermined frequency of processing for the component, for example, the component may be identified to be processed at regular time intervals. Identifying components to be processed may be one example of monitoring medical device conditions, as described at 202 of FIG. 2. The IMS may indicate the component or components to be processed by adjusting a status of the component within a memory of the IMS to "processing requested".

At 304, method 300 may include locking the medical device from being used. The IMS may send a signal to the medical device via a wired or wireless connection that powers off the device and preventing the device from being powered on until after processing is complete, in one example. The signal may close programs and prevent reopening of programs until processing is complete. In another example, the signal may cause the medical device to display a message on a display of the device indicating processing may be in progress and where the message might not be navigated away from until processing is complete, and so on.

At 306, method 300 includes dispatching a robot processing system to the medical device. For example, when the medical device is in a patient room, the robot may be dispatched from a docking station where the robot is stored to the patient room. In other examples, the medical device may be removed from the patient room to a processing area where the robot is stationed.

At 308, method 300 includes indicating the component to be processed to the processing robot. This may include sending a signal via wireless communication from the IMS to the robot that has been dispatched to the medical device at 306, indicating the component of the medical device for which processing has been requested. The second part 350 of method 300 for detecting and interpreting VDIs and processing device components based on VDIs as executed by the robot is described in FIG. 3B.

At 322 of FIG. 3B, the second part 350 of method 300 includes scanning a VDI of the component to be processed to determine an appropriate processing level for the component. The robot may have stored in its memory a reference indicating which processing level is indicated by each possible VDI. For example, multiple VDI types may be used to indicate each of the five types of processing described above. The robot may refer to the reference to determine a processing level indicated by the VDI. For example, if the VDI is a green color on the surface of a component of the device, the VDI may indicate high level disinfection.

Once the appropriate processing level has been determined for the component at 322, at 324, method 300 includes processing the component. The component may be processed according to a processing method stored in the memory of the processing system robot associated with the determined processing level. For example, if the VDI indicates high level disinfection, the robot may apply a disinfecting wipe to the surface of the component.

At 326, method 300 includes checking the component for sufficient processing. For example, the robot may scan the component with a UV light to determine bacterial contamination of the component.

At 328, method 300 includes determining if processing is sufficient. Sufficient processing may be determined based on a scan or other check conducted at 326. If at 328, it is determined processing is not sufficient, method 300 may return to 324 to process the component again using the method associated with the processing level determined at 322.

If at 328 it is determined processing is sufficient for the component, method 300 proceeds to 330. At 330, method 300 includes indicating to the IMS that the component is processed. For example, this may include sending a signal or other informational indicator from the processing robot to the IMS, indicating that the component has been processed by the robot. The signal may further indicate that it has been determined the component has undergone sufficient processing such that contamination of the component is low, e.g., below a non-zero positive contamination threshold. This may indicate that there is low risk of contamination of a user or patient who may be in contact with the component.

At 310 of the first part 340 of method 300, the IMS may receive a component processing status from the processing robot (e.g., sent to the IMS from the processing robot as described at 330 of FIG. 3B). The IMS may in turn update a status of the component to indicate the component has been processed, for example, changing a status of the component from "processing requested" to "processed". This may include recording a date/time at which the component is indicated to have been processed such that a predetermined frequency of processing events may be maintained.

Both the first part 340 and the second part 350 of method 300 may proceed to determine if additional processing is requested, which may be indicated by at least one of the IMS and the processing robot. For example, at 312 of the first part 340, method 300 as executed by the IMS includes determining if additional processing is requested. This may include reviewing a status of all components of the medical device to determine if any components have a status of "processing requested". If it is determined that additional processing is requested, the first part 340 of method 300 proceeds to 314 and includes maintaining the processing robot dispatched to the medial device. Method 300 may return to 308, where the method 300 includes indicating a component to be processed to the processing robot.

The second part 350 of method 300, as executed by the processing robot, includes, at 332, determining if additional processing is requested. Processing of additional components of the device may be requested, for example, as indicated by a component status in the IMS, as described above. In another example, the robot may perform a scan using UV light over the surface of the medical device to detect any potential contaminated components. If a contaminated component is detected, the robot may indicate additional processing is requested and method 300 may return to 322 to scan VDI of the contaminated component. The second part 350 of method 300 then proceeds to determine a processing level of the contaminated component and process the contaminated component. This cycle may be repeated until, at 332, it is indicated no additional processing is requested. Additional processing may not be requested when, for example, a status of all components of the medical device are "processed" or, based on the UV scan by the robot, components of the device might be uncontaminated.

If at 332 it is determined that additional processing is not requested, at 334, method 300 includes indicating to the IMS that the medical device has been processed. For example, if the robot determines all components for which processing has been requested have been processed and processed sufficiently, the robot may send a signal to the IMS (e.g., received by the IMS as described at 315 of the first part 340 of method 300) indicating the medical device in its entirety has been processed and may be uncontaminated.

At 315 of the first part 340 of method 300, the IMS may receive a medical device processing status from the processing robot (e.g., sent to the IMS from the processing robot as described at 334 of FIG. 3B). The IMS may in turn update a status of the medical device to indicate the medical device has been processed, for example, changing a status of the medical device from "processing requested" to "processed". This may include recording a date/time at which the medical device is indicated to have been processed such that a predetermined frequency of processing events may be maintained.

As described at 316 of the first part 340, method 300 as executed by the IMS may include recalling the processing robot. At 336 of the second part 350, method 300 as executed by the processing system robot may include receiving recall instruction from the IMS (e.g., 316 of the first part 340) and returning the robot to the docking, which may be a location where the robot is stored and or charged and may be a location other than in proximity to the medical device and/or in proximity to patients. Method 300 as executed by the processing system robot (e.g., the second part 350) ends.

At 318 of the first part 340 as executed by the IMS, method 300 may include indicating components of the medical device and the medical device itself have been processed. This may include updating a status of the medical device in IMS memory to "processed" and recording a date/time at which the medical device is indicated to have been processed such that a predetermined frequency of processing events may be maintained.

At 320, method 300 may include unlocking the medical device. For example, the IMS may send a signal to the medical device via a wired or wireless connection that powers on the device, in one example. The signal may allow opening of data-collection programs. In another example, the signal may cause the medical device to display a message on the display of the device indicating processing may be complete, and so on. Method 300 ends.

In this way, detection and interpretation of VDIs for components of medical devices and processing of the medical devices may be automatically conducted without user input. Benefits of the method 300 as described in FIGS. 3A-3B may include higher processing accuracy (e.g., less user error) and a reduced amount of time spent by medical providers processing medical devices, providing medical providers with more time for patient care.

Some medical settings may not easily accommodate a robot or fleet of robots autonomously dispatched to process medical devices. In this case, it may be more resource efficient (e.g., cost, time, space, and so on), for users to process medical devices. FIG. 4 expands on method 200 of FIG. 2 and describes an example method 400 where processing a medical device based on VDIs of components of the medical device includes using an IMS (e.g., the IMS 103 of FIG. 1A) and a user processing system, where the user uses a handheld imaging system (e.g. the smartphone 107 of FIG. 1A) with an application (e.g. the application 109 of FIG. 1A) for detecting and interpreting VDIs. The user may then use an output of VDI interpretation by the application to direct processing of components of the medical device.

The IMS may maintain a record of processing statuses for each component of the medical device, as well as the medical device itself. In one example, the IMS may maintain a record for a single medical device or for multiple medical device and be in communication with one smartphone/application or multiple smartphones/applications. In another example, a device other than a smartphone may be used to run the application, for example, any device with an image processing system, including a camera for capturing images of the medical device, a memory for storing information (e.g., a reference describing processing levels indicated by VDIs), a means for communicating with the IMS, and a display screen. Method 400 is described as implemented by the smartphone application.

Method 400 may be employed upon determining that processing of components of the medical device has been requested, for example, as described at 204 of FIG. 2. At 402, method 400 includes imaging the medical device. For example, the application may use the smartphone camera to capture images of the medical device. In one example, still images of the medical device may be captured and multiple images may be captures to include all components of the medical device in the images. In another example, the application may use the smartphone camera to capture images in real time, for example, where the app displays camera output in real time on the display of the smartphone (e.g., image rendering device 199 of FIG. 1D).

At 408, method 400 includes identifying VDIs of the medical device. For example, the application may detect VDIs in images captured at 402. In one example, identified VDIs may be highlighted in the application, for example, the application may use virtual and/or augmented reality methods to overlay a color or symbol of the VDI on the image(s) of the actual device to make the color brighter or the symbol larger to capture a user's attention.

At 410, method 400 includes determining a processing level requested by VDIs of the medical device. For example, the application may include a reference guide indicating which processing level may be indicated by a VDI. For a component that may have multiple VDIs (e.g., a color and a tag), the application may determine if the VDIs indicate the same processing level or different processing levels.

At 412, method 400 includes applying labels to the medical device images (e.g., generated at 402) to indicate appropriate processing levels for components of the medical device. When still images are generated at 402, at 412, the application may overlay labels on components captured in the image which are configured with VDIs. When real-time images are generated at 402, at 412, the application may overlay labels on components displayed on the screen, or may overlay labels on displayed components when the component is selected by a user.

For both still images and real-time images, labels added to the images may be a text label or other indicator describing the processing level indicated by the VDI of the component. For example, if the component VDI is a color, the application may label the component on the image of the component by outlining the component and overlaying text indicating a corresponding processing level or overlaying an image indicating the processing level. The label may be interactive such that, when the label is selected by a user, the application may display further information about the processing level, for example, processing agents which may be used to process the component, a duration for processing the component which may result in sufficient processing, and so on. Method 400 ends.

From labels added to images of the medical devices, the user may read information indicating an appropriate processing label, which may include a processing agent or other processing method, and process the method accordingly. Using the application to identify and interpret VDIs of components of the medical device may allow users to quickly and accurately process components of the medical device, which may reduce a time the medical device is out of rotation compared to conventional methods where the user may identify and interpret VDIs manually by referring to a user manual, for example.

In this way, VDIs may be implemented on components of medical devices, such as an ultrasound imaging system, to indicate an appropriate processing level of a component. Appropriate processing levels may be different for different component of medical devices based on component, use, use frequency, materials, and so on. Labeling components of the medical devices with VDIs may be a simple and clear method for indicating appropriate processing levels for different components, which may reduce a time, cost, and complexity of methods for processing medical devices. VDIs may be detected and interpreted by a variety of users, for example, a human user or a robot user. The users may use tools, such as smartphone applications, sensors, or information from an IMS to determine which components of the medical device are requested to be processed. The users may then detect and interpret VDIs and use information about processing level of components indicated by the VDIs to process components of the medical device. Information about a level of processing for various components of the medical device may be quickly and easily conveyed to the user, reducing user error during processing; reducing costs associated with over processing or damaging components; reducing time spent by a user determining a processing level for the medical device and processing the medical device; and so on. The methods and systems described herein may also allow a safer use of the system (e.g., less risk of contamination to the user and patient) as the VDIs may indicate to the user which parts of the equipment can be safely touched during use.

FIGS. 1A-1D shows an example configuration with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

While the above description illustrates the VDIs on or integrated with actual surfaces of the physical manifestation of a medical device, such as an ultrasound machine, aspects may be applied in instructions or displays that depict the medical device in a pictorial manner. For example, displaying an image of the medical device may enable inclusion of VDI elements at appropriate locations in the pictorial display, for example via an augmented reality display of the physical medical device with an overlay of the VDIs on the screen at the appropriate screen locations to correspond to the surfaces and indicate the appropriate level of processing. Thus, as used herein, displaying an ultrasound device may include physical display of the physical manifestation, as well as display on a screen of a video or image rendering device. The image rendering device may include a processor and camera, where instructions stored in the memory process the image and identify the medical device being captured by the camera, and segment the image into various components of the device (e.g., components of an ultrasound system). The image segmentation may identify the components and display an outline of the various components overlaid on the displayed image of the device, and thus augmenting the image. Further, within the outline, the system may further provide processing levels (e.g., numbers as one example) based on querying a database that provides a correlation of the processing level of particularly identified components. In this way, the augmented displayed image may indicate to a user the requested processing levels of the different components directly on the display of the components.

The disclosure also provides support for a method comprising: displaying an ultrasound device having a first component with a first visual indicator to indicate a first processing level and a second component with a second visual indicator to indicate a second processing level. In a first example of the method, the ultrasound device is displayed on an image rendering device. In a second example of the method, optionally including the first example, the image rendering device provides an augmented reality view, where the first visual indicator and the second visual indicator are provided only via an augmented reality overlay on a display of the image rendering device. In a third example of the method, optionally including one or both of the first and second examples, the first visual indicator and the second visual indicator are permanent visually detectable indicators (VDIs) that convey information about cleaning, disinfection, and sterilization (CDS) of touchable components on the ultrasound device. In a fourth example of the method, optionally including one or more or each of the first through third examples, the method further comprises: processing the first component to the first processing level that is different than the second processing level, and processing the second component to the second processing level. In a fifth example of the method, optionally including one or more or each of the first through fourth examples, the method further comprises: operating an automated processing machine for processing the first component to the first processing level and the second component to the second processing level, the automated processing machine configured with an image processing system to identify and interpret the VDIs and further configured with a processing apparatus for processing components according to a processing level indicated by the respective VDI. In a sixth example of the method, optionally including one or more or each of the first through fifth examples, the VDIs are implemented at surfaces of the ultrasound device and include color coding. In a seventh example of the method, optionally including one or more or each of the first through sixth examples, the VDIs are implemented at surfaces of the ultrasound device and include patterns. In an eighth example of the method, optionally including one or more or each of the first through seventh examples further wherein the VDIs cover respective surfaces of the respective components completely. In a ninth example of the method, optionally including one or more or each of the first through eighth examples further wherein the VDIs cover respective surfaces of the respective components partially.

The disclosure also provides support for an ultrasound device, including a first component with a first visual indicator to indicate a first processing level, and a second component with a second visual indicator to indicate a second processing level. In a first example of the system, the first visual indicator and the second visual indicator are permanent visually detectable indicators (VDIs) implemented at surfaces of the ultrasound device and include color coding and patterns. In a second example of the system, optionally including the first example, the VDIs include five distinct VDIs each corresponding to one of five distinct processing levels. In a third example of the system, optionally including one or both of the first and second examples, the five processing levels include: cleaning, low level disinfection, intermediate level disinfection, high level disinfection, and sterilization. In a fourth example of the system, optionally including one or more or each of the first through third examples, the first component and the second component are each individual elements of the ultrasound device. In a fifth example of the system, optionally including one or more or each of the first through fourth examples, the first component and the second component are each a distinct group of elements of the ultrasound device, where elements are grouped according to a use, use frequency, or surface material.

The disclosure also provides support for a method for processing an ultrasound device, including processing a first surface to a first processing level as indicated by a first permanent visual indicator, and processing a second surface to a second processing level as indicated by a second permanent visual indicator. In a first example of the method, the first processing level is different than the second processing level. In a second example of the method, optionally including the first example, the ultrasound device is processed by a user or by an automated processing machine. In a third example of the method, optionally including one or both of the first and second examples, the method further comprises: after the ultrasound device has been processed, indicating the ultrasound device has been processed.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," and so on. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A method comprising:
identifying a first visual indicator of a first component of an ultrasound imaging system, the first visual indicator indicating a first processing level;
identifying a second visual indicator of a second component of the ultrasound imaging system, the second visual indicator different from the first visual indicator, and the second visual indicator indicating a second processing level; and
displaying the ultrasound device having the first component with the first visual indicator to indicate the first processing level and having the second component with the second visual indicator to indicate the second processing level, the displaying based on the respective identifications of the first visual indicator and the second visual indicator, wherein the first component and the second component are each individual elements of the ultrasound device.
2. The method of claim 1, wherein the ultrasound device is displayed on an image rendering device.
3. The method of claim 2, wherein the first visual indicator and the second visual indicator are visually detectable indicators (VDIs) that convey information about cleaning, disinfection, and sterilization (CDS) of touchable components on the ultrasound device.
4. The method of claim 3, wherein the VDIs include one or more of color coding, patterns, and visually different materials on surfaces of components.
5. The method of claim 4, wherein respective VDIs completely cover respective surfaces of respective components.
6. The method of claim 4, wherein respective VDIs only partially cover respective surfaces of respective components.
7. The method of claim 3, wherein respective VDIs used for each component of the ultrasound device indicate respective levels of processing for the respective components, where different components of the ultrasound device have different levels of processing.
8. The method of claim 1, wherein the individual elements are coupled to one another to form a single unitary structure that is configured to be moved as a single system from room to room.
9. A method comprising:
displaying an ultrasound device having a first component with a first visual indicator to indicate a first processing level and a second component with a second visual indicator to indicate a second processing level, wherein the ultrasound device is displayed on an image rendering device, wherein the image rendering device provides an augmented reality view, and wherein the first visual indicator and the second visual indicator are provided only via an augmented reality overlay on a display of the image rendering device.
10. The method of claim 9, wherein the first visual indicator and the second visual indicator are permanent visually detectable indicators (VDIs) that convey information about cleaning, disinfection, and sterilization (CDS) of touchable components on the ultrasound device.
11. The method of claim 10, further comprising processing the first component to the first processing level that is different than the second processing level, and processing the second component to the second processing level.
12. The method of claim 11, wherein the VDIs are implemented at surfaces of the ultrasound device and include color coding.
13. The method of claim 11, wherein the VDIs are implemented at surfaces of the ultrasound device and include patterns.
14. The method of claim 10, wherein the VDIs cover respective surfaces of the respective components completely.
15. The method of claim 10, wherein the VDIs cover respective surfaces of the respective components partially.
16. A method comprising:
displaying an ultrasound device having a first component with a first visual indicator to indicate a first processing level and a second component with a second visual indicator to indicate a second processing level, wherein the ultrasound device is displayed on an image rendering device, wherein the first visual indicator and the second visual indicator are permanent visually detectable indicators (VDIs) that convey information about cleaning, disinfection, and sterilization (CDS) of touchable components on the ultrasound device;
processing the first component to the first processing level that is different than the second processing level, and processing the second component to the second processing level; and
operating an automated processing machine for processing the first component to the first processing level and the second component to the second processing level, the automated processing machine configured with an image processing system to identify and interpret the VDIs and further configured with a processing apparatus for processing components according to a processing level indicated by the respective VDI.

* * * * *